(12) United States Patent
Amamiya et al.

(10) Patent No.: US 10,429,332 B2
(45) Date of Patent: Oct. 1, 2019

(54) OIL DEGRADATION METER AND METHOD FOR EVALUATING OIL DEGRADATION

(71) Applicant: ATAGO CO., LTD, Tokyo (JP)

(72) Inventors: Hideyuki Amamiya, Tokyo (JP); Akihito Kubota, Saitama (JP)

(73) Assignee: ATAGO CO., LTD, Tokyo (JP)

( * ) Notice: Subject to any disclaimer, the term of this patent is extended or adjusted under 35 U.S.C. 154(b) by 0 days.

(21) Appl. No.: 15/508,249

(22) PCT Filed: May 15, 2015

(86) PCT No.: PCT/JP2015/064074
§ 371 (c)(1),
(2) Date: Mar. 2, 2017

(87) PCT Pub. No.: WO2016/185524
PCT Pub. Date: Nov. 24, 2016

(65) Prior Publication Data
US 2017/0276629 A1    Sep. 28, 2017

(51) Int. Cl.
G01N 33/03 (2006.01)
G01N 27/22 (2006.01)
G01N 33/28 (2006.01)

(52) U.S. Cl.
CPC ........... G01N 27/221 (2013.01); G01N 33/03 (2013.01); G01N 33/2805 (2013.01)

(58) Field of Classification Search
CPC ... G01N 27/221; G01N 33/03; G01N 33/2805
See application file for complete search history.

(56) References Cited

U.S. PATENT DOCUMENTS

| 4,646,070 A | 2/1987 | Yasuhara et al. |
| 5,594,327 A * | 1/1997 | Sagredos ............... G01N 27/06 324/439 |

(Continued)

FOREIGN PATENT DOCUMENTS

| CN | 1459630 | 12/2003 |
| CN | 101949877 A | 1/2011 |

(Continued)

OTHER PUBLICATIONS

Kazuaki Ichikawa, "Evaluation of Heat-deteriorated Edible Oils—Relationship between PV/CV/AV Values and Polar Compounds Content—", Journal of Nagoya Bunri University, No. 12, 2012, pp. 121-130.

(Continued)

Primary Examiner — Akm Zakaria
(74) Attorney, Agent, or Firm — Greenblum & Bernstein, P.L.C.

(57) ABSTRACT

An oil degradation meter and a method for evaluating oil degradation are provided, in which a user is enabled to arbitrarily set a degradation of oil/fat using an acid value (AV value) as an index, and capable of learning a replacement time of oil/fat easily with a stable reproducibility, even in a case where a condition such as a moisture amount in food (deep-fried food) is different. In a setup procedure, an acid value ($AV_0$) of unused oil/fat is set to 0, a dielectric constant ($D_0$) at that time is measured and recorded, a dielectric constant ($D_{100}$) of oil/fat at a replacement time under a specific oil/fat usage condition is measured, and it is recorded along with an acid value ($AV_{100}$) at that time, and in a measurement procedure, a dielectric constant ($D_n$) of the sample oil/fat is measured, and an acid value ($AV_n$) of said sample oil/fat is calculated based on the dielectric constants ($D_0$, $D_{100}$) and the acid value ($AV_{100}$) recorded in said setup (Continued)

procedure, according to a calculation formula of $[AV_n=AV_{100}\times\{(D_n-D_0)/(D_{100}-D_0)\}]$.

4 Claims, 2 Drawing Sheets

(56) References Cited

U.S. PATENT DOCUMENTS

| | | | |
|---|---|---|---|
| 6,449,580 B1 * | 9/2002 | Bardetsky | G01N 33/2888 702/127 |
| 6,469,521 B1 | 10/2002 | Klün et al. | |
| 2005/0222783 A1 | 10/2005 | Muhl et al. | |
| 2010/0052702 A1 | 3/2010 | Ju et al. | |
| 2012/0206253 A1 * | 8/2012 | Taniguchi | G01N 33/2835 340/438 |
| 2015/0027205 A1 | 1/2015 | Brugger | |

FOREIGN PATENT DOCUMENTS

| | | |
|---|---|---|
| CN | 103293201 A | 9/2013 |
| JP | 58-85314 | 5/1983 |
| JP | 63-195555 | 8/1988 |
| JP | 63-200051 | 8/1988 |
| JP | 2010-510486 | 4/2010 |
| JP | 2014-214663 | 11/2014 |
| WO | 2013/139354 | 9/2013 |

OTHER PUBLICATIONS

Qin Wen, Xue Wen-tong, "Nondestructive measurment of soybean oil quality with dielectric property", Journal of China Agricultual University, 2009, 14(3), pp. 113-117.

Office Action issued in Taiwan Counterpart Patent Appl. No. 104120113, dated Mar. 17, 2016.
Search Report issued in International Bureau of WIPO Patent Application No. PCT/JP2015/064074, dated Jul. 28, 2015.
Jan. 30, 2019 extended European Search Report issued in counterpart European Application No. 15892524.8.
Mar. 18, 2019 Chinese Office Action in corresponding Chinese Application No. 201580049990.0.
Mar. 18, 2019 Third Party Submission in corresponding European Application No. 15892524.8.
"Technology for Monitoring Automotive Engine Lubricating Oil by Dielectric Constant Method" by Li Xiwu et al. published in the vol. 46, No. 5 of the Jounal of Southwest Jiaotong University, pp. 831-835, Oct. 2011.
"Vehicle lubrication oil on-line monitoring method and monitoring system" by Liu Yu-mei et al., in vol. 39, No. 6 of Journal o f Jilin University (Engineering and Technology Edition), pp. 1441-1445, Nov. 2009.
"Changes in Physical and Chemical Properties of Shortenings Used for Commercial Deep-Fat Frying" by L.M. Smith et al. in vol. 63, No. 8 of JAOCS, pp. 1017-1023, Aug. 1986.
"Effects of Sugar, Salt, and Water on Soybean Oil Quality During Deep Frying" by Yan-Hwa Chu et al. in vol. 71, No. 8 of JAOCS, pp. 897-900, Aug. 1994.
"A Comparative Study of Analytical Methods for Quality Evaluation of Frying Fat" by L.B. Croon et al. in vol. 88, no. 3 of Fette, Seifen, Anstrichmittel, pp. 87-91, 1986.
"Chemical and physical parameters as quality indicators of used frying fats" by Christian Gertz in vol. 102, pp. 566-572 of Eur. J. Lipid Sci. Technology, pp. 566-572, 2000.
Wikipedia article entitled "Correlation coefficient" last edited on Feb. 25, 2019, pages 1 and 2, https://en.wikipedia.org/wiki/Correlation_coefficient.

* cited by examiner

OIL DEGRADATION METER AND METHOD FOR EVALUATING OIL DEGRADATION

TECHNICAL FIELD

The present invention relates to an oil degradation meter and a method for evaluating oil degradation for evaluating a state of oil/fat.

BACKGROUND ART

As an index for a refinement and an alteration (degradation) of edible oil and fat, total polar materials (referred hereafter as "TPM value"), an acid value (referred hereafter as "AV value"), etc. are used.

The TPM value uses an amount of total polar materials (TPM), which is a generic name of a free fatty acid that is generated by moistures in food (deep-fried food), an aromatic compound that is increased by heating, and a material that is produced by oxidation due to contact with air, etc., as an index. This TPM value can be derived from a measurement result of a dielectric constant of oil/fat.

The AV value is defined by an amount (mg) of kalium hydroxide (KOH) that is required in neutralizing free fatty acids existing in 1 g of edible oil and fat.

Note that the TPM value is used as an index in Europe, whereas the AV value is used as an index in Japan.

PRIOR ART DOCUMENTS

Non-Patent Documents

Non-Patent Document 1: Kazuaki Ichikawa, "Evaluation of Heat-deteriorated Edible Oils—Relationship between PV/CV/AV Values and Polar Compounds Content—", Journal of Nagoya Bunri University, No. 12 (2012), pp. 121-130.

SUMMARY OF THE INVENTION

Problems to be Solved by the Invention

By the way, a measurement of the TPM value is easy because a dielectric constant of oil/fat can be obtained easily by a measurement of an impedance of oil/fat. In contrast to that, a measurement of an amount of kalium hydroxide that is required in neutralizing free fatty acids is not easy because it must be done by a neutralization titration.

Then, there is no correlation between the dielectric constant of oil/fat and the AV value, so that it would become a totally different value depending on a condition such as a moisture amount in food (deep-fried food), etc. For this reason, in the case of using the AV value as an index, there is a current state in which oil/fat is replaced by finding out an empirical limit point from a color, an odor, etc. of oil/fat, because the measurement of the AV value is not easy.

Therefore, the present invention is proposed in view of the above mentioned situations, and has an object of providing an oil degradation meter and a method for evaluating oil degradation, in which a user is enabled to arbitrarily set a degradation of oil/fat using an acid value (AV value) as an index, and capable of learning a replacement time of oil/fat easily with a stable reproducibility, even in a case where a condition such as a moisture amount in food (deep-fried food) is different.

Means for Solving the Problems

In order to solve the above described problems and achieve the above noted object, the oil degradation meter according to the present invention has the following configuration,

[Configuration 1]

It is characterized by having: a dielectric constant measuring means for measuring a dielectric constant of sample oil/fat; a memory means for storing the dielectric constant measured by said dielectric constant measuring means; an input means for inputting an acid value, and storing the inputted acid value in said memory means; a calculation means for carrying out a calculation based on the dielectric constant and the acid value stored in said memory means; and a control means for controlling said dielectric constant measuring means, said input means, said memory means and said calculation means; wherein said control means, in a setup mode, sets an acid value ($AV_0$) of unused oil/fat to 0, measures a dielectric constant ($D_0$) at that time, stores it in said memory means, measures a dielectric constant ($D_{100}$) of oil/fat at a replacement time under a specific oil/fat usage condition, and stores it along with an acid value ($AV_{100}$) at that time in said memory means; and wherein said control means, in a measurement mode, measures a dielectric constant ($D_n$) of the sample oil/fat, stores this measurement result ($D_n$) in said memory means, and calculates an acid value ($AV_n$) of said sample oil/fat based on the dielectric constants ($D_0$, $D_{100}$) and the acid value ($AV_{100}$) stored in said memory means in said setup mode, according to a calculation formula of $[AV_n = AV_{100} \times \{(D_n - D_0)/(D_{100} - D_0)\}]$ by using said calculation means.

[Configuration 2]

It is characterized in that the acid value ($AV_{100}$) of oil/fat at the replacement time is defined as 100, in the oil degradation meter having the configuration 1.

Then, the method for evaluating oil degradation according to the present invention has the following configuration.

[Configuration 3]

It is characterized in that: in a setup procedure, setting an acid value ($AV_0$) of unused oil/fat to 0, measuring and recording a dielectric constant ($D_0$) at that time, measuring a dielectric constant ($D_{100}$) of oil/fat at a replacement time under a specific oil/fat usage condition, and recording it along with an acid value ($AV_{100}$) at that time; and in a measurement procedure, measuring a dielectric constant ($D_n$) of the sample oil/fat, and calculating an acid value ($AV_n$) of said sample oil/fat based on the dielectric constants ($D_0$, $D_{100}$) and the acid value ($AV_{100}$) recorded in said steep procedure, according to a calculation formula of $[AV_n = AV_{100} \times \{(D_n - D_0)/(D_{100} - D_0)\}]$.

[Configuration 4]

It is characterized in that the acid value ($AV_{100}$) of oil/fat at the replacement time is defined as 100, in the method for evaluating oil degradation having the configuration 3.

Effects of the Invention

In the oil degradation meter according to the present invention, in a setup mode, an acid value ($AV_0$) and a dielectric constant ($D_0$) of unused oil/fat are stored, and an acid value ($AV_{100}$) and a dielectric constant ($D_{100}$) of oil/fat at a replacement time under a specific oil/fat usage condition are stored, and in a measurement mode, a dielectric constant ($D_n$) of the sample oil/fat is measured, and an acid value ($AV_n$) of the sample oil/fat is calculated according to a calculation formula of $[AV_n=AV_{100} \times \{(D_n-D_0)/(D_{100}-D_0)\}]$.

Also, in the method for evaluating oil degradation according to the present invention, in a setup procedure, an acid value ($AV_0$) and a dielectric constant ($D_0$) of unused oil/fat are recorded, and an acid value ($AV_{100}$) and a dielectric constant ($D_{100}$) of oil/fat at a replacement time under a specific oil/fat usage condition are recorded, and in a measurement procedure, a dielectric constant ($D_n$) of the sample oil/fat is measured, and an acid value ($AV_n$) of the sample oil/fat is calculated according to a calculation formula of $[AV_n=AV_{100} \times \{(D_n-D_0)/(D_{100}-D_0)\}]$.

Also, when the acid value ($AV_{100}$) of oil/fat at the replacement time is defined as 100, a percentage to the replacement time is calculated from the measured dielectric constant ($D_n$) of the sample oil/fat.

Therefore, in the oil degradation meter and the method for evaluating oil degradation according to the present invention, it is possible to learn the replacement time of oil/fat, based on a measured numerical value of a dielectric constant that is objective and highly reliable, by converting it into an acid value.

Namely, the present invention is capable of providing an oil degradation meter and a method for evaluating oil degradation, in which a user is enabled to arbitrarily set a degradation of oil/fat using an acid value (AV value) as an index, and capable of learning a replacement time of oil/fat easily with a stable reproducibility, even in a case where a condition such as a moisture amount in food (deep-fried food) is different.

DETAILED DESCRIPTION OF THE INVENTION

In the following, embodiments of an oil degradation meter and a method for evaluating oil degradation according to the present invention will be described with references to the drawings.

[Outline of a Configuration of an Oil Degradation Meter According to the Present Invention]

Figure 1:
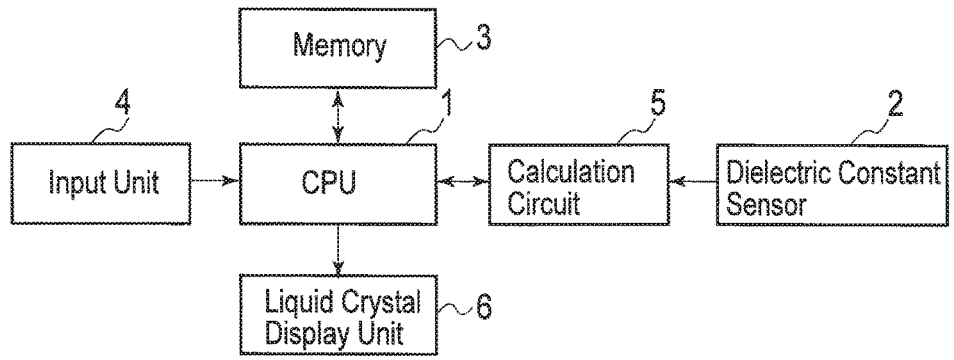
FIG. 1 is a block diagram showing a configuration of an oil degradation meter according to the present invention.

FIG. 1 is a block diagram showing a configuration of an oil degradation meter according to the present invention.

This oil degradation meter is a device for measuring a dielectric constant of sample oil/fat, and calculating an AV value (acid value) from this measurement result.

As shown in FIG. 1, this oil degradation meter has a CPU 1 that constitutes a control means. This CPU 1 controls a dielectric constant sensor 2 that constitutes a dielectric constant measuring means. The dielectric constant sensor 2 has comb electrodes to be immersed into the sample oil/fat, such that an impedance of the sample oil/fat can be measured from a change in frequency by applying AC voltage between these comb electrodes. From this impedance measurement result, it is possible to calculate the dielectric constant of the sample oil/fat.

Also, the CPU 1 controls an input unit 4 that constitutes an input means, and processes input signals from this input unit 4. To the input unit 4, it is possible to input various numerical values and commands for operation mode selection, etc., besides the AV values (acid values).

Then, the CPU 1 controls a memory 3 that constitutes a memory means. The memory 3 stores a dielectric constant measured by the dielectric constant sensor 2, an inputted AV value (acid value), and other various numerical values.

Also, the CPU 1 controls a calculation circuit 5 that constitutes a calculation means. The calculation circuit 5 carries out a calculation based on dielectric constants and AV values (acid values) stored in the memory 3, and other various calculations.

Further, a liquid crystal display unit 6 is connected to the CPU 1. The liquid crystal display unit 6 displays various types of information such as an AV value (acid value) inputted by a user of this device, other various numerical values, calculation results by the calculation circuit 5, etc.

[A Method for Evaluating Oil Degradation According to the Present Invention (an Operation of the Oil Degradation Meter)]

Figure 2:
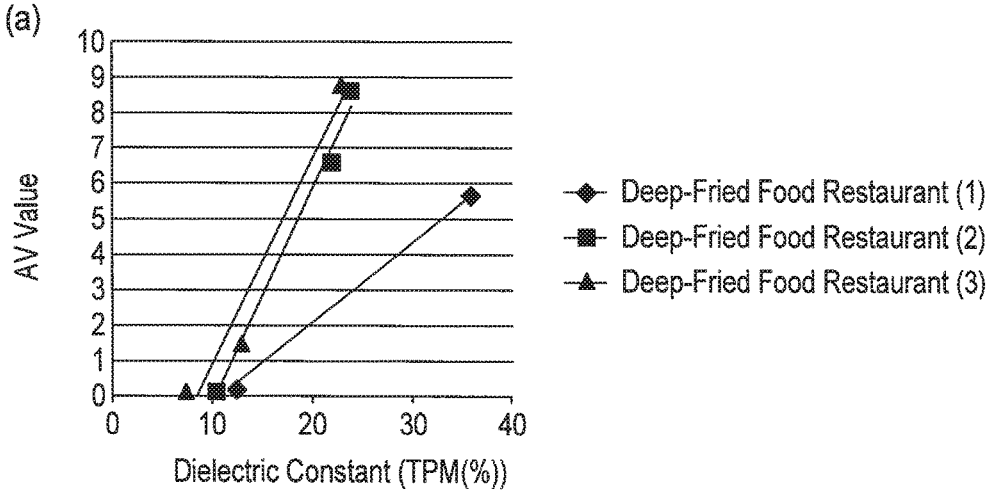
FIG. 2 is a graph showing a relationship between a dielectric constant and an acid value (AV value) of oil/fat.
Figure 2:
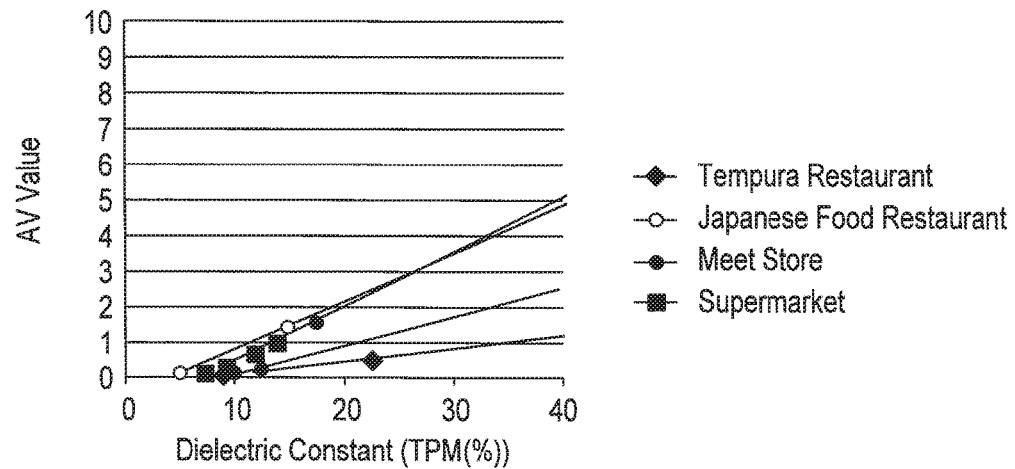

FIG. 2 is a graph showing a relationship between a dielectric constant and an acid value (AV value) of oil/fat.

A part (a) of FIG. 2 is a graph showing a relationship between a dielectric constant and an acid value (AV value) of oil/fat at a deep-fried food restaurant (1), a deep-fried food restaurant (2) and a deep-fried food restaurant (3).

A part (b) of FIG. 2 is a graph showing a relationship between a dielectric constant and an acid value (AV value) of oil/fat at a tempura restaurant, a Japanese food restaurant, a meat store, and a supermarket.

Note that, in FIG. 2, the horizontal axis indicates a TPM value, and this TPM value is a value that is correlated with the dielectric constant of oil/fat. Therefore, this FIG. 2 is showing a relationship between a dielectric constant and an acid value (AV value) of oil/fat.

As shown in FIG. 2, the relationship between the dielectric constant and the AV value of oil/fat is different depending on a condition such as a moisture amount in food (deep-fried food) to be dealt with and the like. Namely, when the relationship between the dielectric constant and the AV value is fit to a linear approximation, a slope of a linear approximation equation is different depending on stores. This is supposed to be so because there are differences in types of deep-fried foods and heating times. For example, in the case where an amount to be deep-fried and a frequency for deep-frying are high as in the case of the deep-fried restaurants shown in a part (a) of FIG. 2, a rate by which the AV value is increased with respect to an increase of the dielectric constant is large, and a slope of a linear approximation equation is steep, in comparison with the other stores shown in a part (b) of FIG. 2.

Note that, in a process of degradation of oil/fat, no tendency for an increase of the AV value to be a curve can be observed, so that experimental data of each store can be expressed by a linear approximation. When points off a linear approximation line are looked, there are errors of about ±0.5 or ±1.0 with respect to the AV value. Causes of the errors are supposed to be a precision in the measurement, a fact that data are re-plotted via colors of oil/fat, a fact that usage conditions of oil/fat are not uniform, etc. Even when these errors are taken into account, it can be said that an increase of the AV value in a process of degradation of oil/fat can be expressed by a linear approximation.

Figure 3:
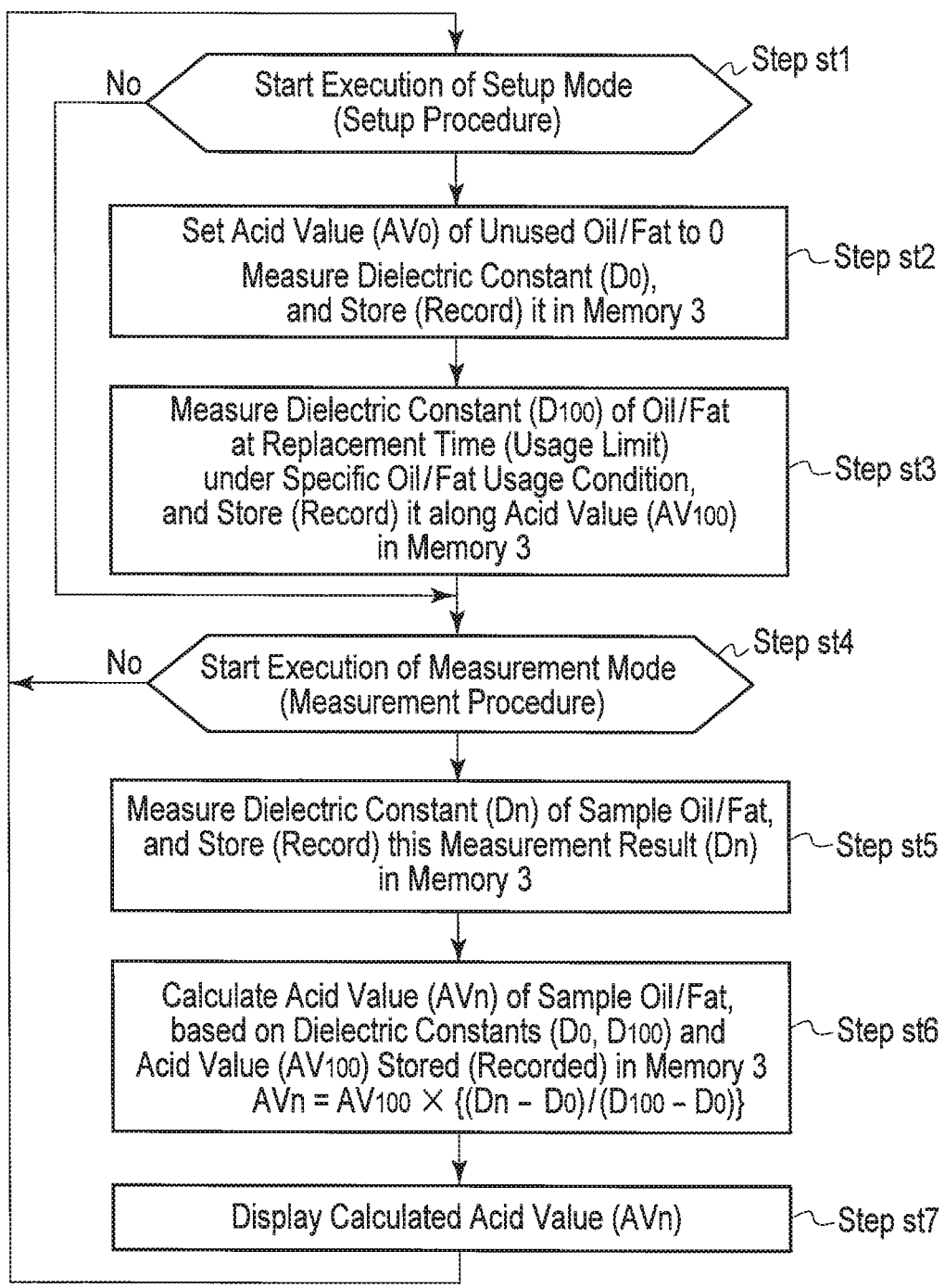
FIG. 3 is a flow chart for explaining a method for evaluating oil degradation according to the present invention.

FIG. 3 is a flow chart for explaining a method for evaluating oil degradation according to the present invention.

This oil degradation meter executes a method for evaluating oil degradation according to the present invention by operating as shown in FIG. 3.

Namely, when a command for a setup mode start is inputted, the CPU 1 starts an execution of a setup mode (setup procedure) at step st1, and proceeds to step st2, where an acid value ($AV_0$) of unused oil/fat is set to 0, a dielectric constant ($D_0$) at that time is measured, and it is stored (recorded) in the memory 3.

Next, it proceeds to step st3, where a dielectric constant ($D_{100}$) of oil/fat at a replacement time (usage limit) under a specific oil/fat usage condition is measured, and it is stored (recorded) along with an acid value ($AV_{100}$) at that time in the memory 3. The acid value ($AV_{100}$) at that time is obtained in advance by a measurement method such as a neutralization titration and the like.

The specific oil/fat usage condition refers to a usage condition of oil/fat at each store such as a deep-fried food restaurant (1), a deep-fried food restaurant (2), a deep-fried food restaurant (3), a tempura restaurant, a Japanese food restaurant, a meat store, and a supermarket, etc., where a usage condition of oil/fat is regarded as constant as long as it is an identical store.

Then, the CPU 1 proceeds to step St4, and when a command for a measurement mode start is inputted, it starts an execution of a measurement mode (measurement procedure), and proceeds to step st5, where a dielectric constant ($D_n$) of the sample oil/fat is measured, and this measurement result ($D_n$) is stored (recorded) in the memory 3.

Next, the CPU 1 proceeds to step St6, and calculates an acid value ($AV_n$) of the sample oil/fat based on the dielectric constants ($D_0$, $D_{100}$) and the acid value ($AV_{100}$) stored (recorded) in the memory 3 in the setup mode, according to the following calculation formula by using the calculation circuit 5.

$$AV_n = AV_{100} \times \{(D_n - D_0)/(D_{100} - D_0)\}$$

Then, the CPU proceeds to step st7, and displays the calculated acid value ($AV_n$) of the sample oil/fat by using the liquid crystal display unit 6.

[Another Example (1) of the Calculation Method]

In this oil degradation meter, it may be made to define the acid value ($AV_{100}$) of oil/fat at the replacement time as 100. In this case, the acid value ($AV_n$) of the sample oil/fat that is calculated from the measured dielectric constant ($D_n$) of the sample oil/fat will be indicating a percentage to the replacement time.

[Another Example (2) of the Calculation Method]

In this oil degradation meter, it may be made to set a scale, by dividing a section between the dielectric constants of oil/fat at the unused state $S_0$ and at the replacement time (usage limit) $S_{100}$ of the sample oil/fat, i.e., a section between the dielectric constant $D_0$ at $S_0$ and the dielectric constant $D_{100}$ at $S_{100}$, into for example 100 equal parts. Note that such a numerical value for dividing into equal parts may not necessarily be 100.

Namely, define 1 degree: $\delta_D$ as follows.

$$1 \text{ degree: } \delta_D = (D_{100} - D_0)/100$$

When the degradation is defined as $A_n$, the degradation $A_n$ can be obtained from the measurement value $D_n$ of the dielectric constant, as follows.

$$A_n = (D_n - D_0)/\delta_D$$

Therefore, $A_n = 0$ if $D_n = D_0$, and $A_n = 100$ if $D_n = D_{100}$.

UTILIZABILITY IN INDUSTRY

The present invention will be applied to an oil degradation meter and a method for evaluating oil degradation for evaluating a state of oil/fat.

EXPLANATION OF REFERENCE NUMERALS

1 CPU
2 Dielectric constant sensor
3 Memory
4 Input unit
5 Calculation circuit

The invention claimed is:

1. An oil degradation meter for displaying an acid value ($AV_n$) of a sample oil/fat without measuring the acid value ($AV_n$) of the sample oil/fat, comprising:
(a) a dielectric constant sensor that measures a dielectric constant of the sample oil/fat;
(b) a memory that stores the dielectric constant of the sample oil/fat measured by said dielectric constant sensor;
(c) an input unit that inputs an acid value into said memory that stores the inputted acid value;
(d) a circuit;
(e) a display; and
(f) a processor that controls said dielectric constant sensor, said input unit, said memory, said circuit, and said display,
(g) wherein said processor, in a setup mode,
sets an acid value ($AV_0$) of unused oil/fat to 0,
obtains from the dielectric constant sensor a dielectric constant ($D_0$) of the unused oil/fat,
stores the obtained dielectric constant ($D_0$) of the unused oil/fat in said memory,
obtains from the dielectric constant sensor a dielectric constant ($D_{100}$) of used oil/fat at a replacement time under a specific oil/fat usage condition, and
stores the obtained dielectric constant ($D_{100}$) of the used oil/fat at the replacement time under the specific oil/fat usage condition along with an acid value ($AV_{100}$) of the used oil/fat at the replacement time under the specific oil/fat usage condition in said memory; and
(h) wherein said processor, in a measurement mode,
controls said dielectric constant sensor to measure a dielectric constant ($D_n$) of the sample oil/fat,
stores the measured dielectric constant ($D_n$) of the sample oil/fat in said memory, and
controls said display to display the acid value ($AV_n$) of the sample oil/fat without measuring the acid value ($AV_n$) based on
the dielectric constants of the unused oil/fat and the used oil/fat at the replacement time under the specific oil/fat usage condition ($D_0$, $D_{100}$) obtained from the dielectric constant sensor in the setup mode,
the acid value of the used oil/fat at the replacement time under the specific oil/fat usage condition ($AV_{100}$) stored in said memory in the setup mode, and
a product of the acid value of the used oil/fat at the replacement time under the specific oil/fat usage condition ($AV_{100}$) and a ratio of i) a difference between the measured dielectric constant of the sample oil/fat measured by the dielectric constant sensor in the measurement mode ($D_n$), and the dielectric constant of the unused oil/fat obtained from the dielectric constant sensor in the setup mode ($D_0$), and ii) a difference between the dielectric constant of the used oil/fat obtained from the dielectric constant sensor at the replacement time under the specific oil/fat usage condition in the setup mode ($D_{100}$), and the dielectric constant of the unused oil/fat obtained from the dielectric constant sensor in the setup mode ($D_0$), determined by the circuit.

2. The oil degradation meter of claim 1, wherein the acid value ($AV_{100}$) of oil/fat at the replacement time is defined as 100.

3. A method of evaluating oil degradation by displaying an acid value ($AV_n$) of a sample oil/fat without measuring the acid value ($AV_n$) of the sample oil/fat on an oil degradation meter, comprising:

in a setup procedure, with the oil degradation meter,
setting an acid value ($AV_0$) of unused oil/fat to 0,
obtaining and recording a dielectric constant ($D_0$) of the unused oil/fat,
obtaining a dielectric constant ($D_{100}$) of used oil/fat at a replacement time under a specific oil/fat usage condition, and
recording the obtained dielectric constant ($D_{100}$) of the used oil/fat at the replacement time under the specific oil/fat usage condition along with an acid value ($AV_{100}$) of the used oil/fat at the replacement time under the specific oil/fat usage condition; and in a measurement procedure, with the oil degradation meter, measuring a dielectric constant ($D_n$) of the sample oil/fat, displaying the acid value ($AV_n$) of the sample oil/fat without measuring the acid value ($AV_n$) based on
the dielectric constants of the unused oil/fat and the used oil/fat at the replacement time under the specific oil/fat usage condition ($D_0$,$D_{100}$)obtained with the oil degradation meter in the setup procedure,
the recorded acid value of the used oil/fat at the replacement time under the specific oil/fat usage condition ($AV_{100}$) recorded in the setup procedure, and
a product of the acid value of the used oil/fat at the replacement time under the specific oil/fat usage condition ($AV_{100}$) and a ratio of i) a difference between the measured dielectric constant of the sample oil/fat measured with the oil degradation meter in the measurement procedure ($D_n$), and the dielectric constant of the unused oil/fat obtained with the oil degradation meter in the setup procedure ($D_0$), and ii) a difference between the dielectric constant of the used oil/fat obtained with the oil degradation meter at the replacement time under the specific oil/fat usage condition in the setup procedure ($D_{100}$), and the dielectric constant of the unused oil/fat obtained with the oil degradation meter in the setup procedure ($D_0$).

4. The method of evaluating oil degradation of claim 3, wherein the acid value ($AV_{100}$) of oil/fat at the replacement time is defined as 100.

* * * * *